United States Patent [19]

White et al.

[11] 3,969,293
[45] July 13, 1976

[54] BASIC ZINC PHOSPHITES

[75] Inventors: Edward Louis White, Freehold; William Ernest Robertson, Trenton; William Heng-Sen Yu, Hightstown, all of N.J.

[73] Assignee: NL Industries, Inc., New York, N.Y.

[22] Filed: Mar. 24, 1975

[21] Appl. No.: 561,276

Related U.S. Application Data

[62] Division of Ser. No. 385,850, Aug. 6, 1973, Pat. No. 3,917,804.

[52] U.S. Cl. ............................. 260/22 CB; 106/292; 260/29.6 S; 260/30.6 R
[51] Int. Cl.² ....................... C09D 3/66; C09D 3/80; C09D 5/02; C09D 5/14
[58] Field of Search ......... 260/22 A, 22 CB, 29.6 S, 260/30.6 R; 423/305; 106/292

[56] References Cited

OTHER PUBLICATIONS

Mellor: Comprehensive Treatise on Inorganic and Theoretical Chemistry, vol. 18 (section 18 consists of pp. 911–920).

*Primary Examiner*—Ronald W. Griffin

[57] ABSTRACT

Novel basic zinc phosphites are described for use as tannin stain inhibitors which can be represented by the formula;

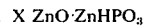

$$X\ ZnO \cdot ZnHPO_3$$

wherein X is a number from ½ to 10.

The basic zinc phosphites are prepared by admixing zinc oxide and phosphorous acid in the presence of water.

3 Claims, No Drawings

BASIC ZINC PHOSPHITES

This application is a division of application Ser. No. 385,850 filed Aug. 6, 1973, now U.S. Pat. No. 3,917,804, issued Nov. 4, 1975.

BACKGROUND OF THE INVENTION

This invention is concerned with novel basic zinc phosphite pigments and their method of preparation. These pigments are useful as tannin stain inhibitors in water and solvent based coating compositions for wood surfaces. The pigments also impart anticorrosive and mildew resistant properties to such coatings.

In the past, lead-based pigments such as basic lead silicate complexes and dibasic lead phosphite have been utilized in paints for inhibiting the tannin staining of wood surfaces such as cedar or redwood which are used extensively in roof and siding coverings for homes and other buildings. These pigments act to prevent the bleeding of tannin or other wood colorant from the wood surface through the coating film which would cause streaking and discoloration and thereby destroy the appearance and quality of the coating. Although the performance of these pigments are highly satisfactory, they suffer from the disadvantage that they are lead-based and therefore ecologically undesirable due to the inherent toxicity of the lead contained therein. As a result, industry is constantly seeking new substitutes for lead containing products which are non-toxic and at the same time exhibit the high performance characteristics of the lead products.

In view of the foregoing, it is an object of this invention to provide a substitute for lead-based tannin stain inhibitor pigments.

It is also an object of this invention to provide novel basic zinc phosphites having excellent efficiency as tannin stain inhibitors for wood surface coatings.

It is a further object of this invention to provide a novel process for preparing said basic zinc phosphites.

SUMMARY OF THE INVENTION

The basic zinc phosphites of this invention can be represented by the emperical formula;

$$X\ ZnO\cdot ZnHPO_3$$

wherein X is a number from ½ to 10. The term "basic" is well known in the art for describing compounds of lead and is used herein in the same context for describing the basic zinc phosphites of this invention. The basicity of the zinc phosphites is related to the molecular ratio of ZnO to $ZnHPO_3$ contained therein. Basicity increases with the ratio; products of high basicity containing higher amounts of ZnO with respect to $ZnHPO_3$. In the above formula, a molecular ratio of ZnO to $ZnHPO_3$ of from ½ to 10 shown which corresponds to a range of basic zinc phosphites from hemibasic to decabasic. The basic zinc phosphites can be substantially anhydrous; that is containing no bound water of hydration or can be associated with about 1 to 3 moles or more of water of hydration. The presence of water of hydration however, is not critical to the performance of the basic zinc phosphites as tannin stain inhibitors. All of the basic zinc phosphite compounds are white solids having slight solubilities in water. When these compositions were tested as tannin stain inhibitors in various latex paint formulations, performance was comparable to a basic lead sulfo-silicate complex.

The process for preparing the basic zinc phosphites of this invention comprises admixing zinc oxide and phosphorous acid in the presence of water to form a basic zinc phosphite wherein the ratio of the number of moles of phosphorous acid to the number of moles of zinc oxide is from 1:1.5 to 1:11.

The zinc oxide and phosphorous acid may be admixed in other ways to form the basic zinc phosphites. For example, the zinc oxide slurry may be slowly added to an aqueous phosphorous acid solution to achieve substantially the same result as above. It is also possible to slowly add dry zinc oxide to an aqueous phosphorous acid solution using strong agitation.

The crude product forms in the slurry as a white solid which can be recovered for example by filtering. The wet product is then dried to remove excess water. If anhydrous basic zinc phosphites are desired the dried product can be heated to remove all water of hydration. By applying this process for the preparation of the basic zinc phosphites excellent yields are obtained.

DESCRIPTION OF THE PREFERRED EMBODIMENTS

The basic zinc phosphites as prepared in this invention having basicities from 1 to 10 have utility as tannin stain inhibitors for water-based coating compositions such as latex paints. When compared to a basic lead sulfo-silicate complex, the basic zinc phosphites show similar tannin stain inhibitory properties. Normal zinc phosphite, $ZnHPO_3$, and zinc oxide alone are essentially ineffective as tannin stain inhibitors. In addition, physical mixtures of zinc oxide and normal zinc phosphite wherein the molar ratio of zinc oxide to normal zinc phosphite is 3:1 which is, on a mole basis, comparable to the chemical compound, tribasic zinc phosphite, are also ineffective.

The preferred tannin stain inhibitors of this invention are those basic zinc phosphites having basicities of from tribasic to octabasic. A particularly preferred basic zinc phosphite is tribasic zinc phosphite.

In addition to effective inhibition of tannin staining, the basic zinc phosphites of this invention are useful in coating compositions as anti-corrosive pigments and as mildew preventive pigments. In flammable materials such as polyester plastics, the basic zinc phosphites impart flame retardancy. Another useful property of many of the basic zinc salts is their ability to absorb high energy ultra-violet radiation. This property makes them suitable for use as ultra-violet screening agents for such UV-sensitive materials as polyethylene, polypropylene and polyvinyl chloride-containing products.

In the method for preparing the instant basic zinc phosphite compositions, the amount of water used in forming the zinc oxide and water slurry is not critical. Generally it is preferred to use sufficient water to provide a weight ratio of water to zinc oxide of at least 3:1 to 8:1. If less than a 3:1 ratio is used the slurry tends to become thick and difficult to stir.

Sufficient agitation should be used in forming the slurry in order to achieve a homogeneous dispersion of the zinc oxide. This is preferably accomplished by slowly adding the zinc oxide to water while constantly stirring the slurry until it appears that all the zinc oxide is evenly dispersed. If the zinc oxide is not well dispersed and agglomerates or aggregates of zinc oxide are present, incomplete reaction will take place resulting in low yields and low purities of the basic zinc phosphites formed in the subsequent stages of the process. The zinc oxide slurry may be formed at room temperatures or at elevated temperatures.

The zinc oxide used must be substantially pure. Impure zinc oxides contaminated with other metallic oxides will result in reduced yields and reduced purities of the formed basic zinc phosphites. The zinc oxide preferred in this invention is a French process zinc oxide having a purity of approximately 98–99%.

An acid catalyst while not essential, is preferably employed in the process to insure high yields. The catalyst is added to the zinc oxide-water slurry prior to the addition of phosphorous acid.

Among the acid catalysts which may be used are the water soluble organic carboxylic acids containing at least one carboxylate group. The term, "water soluble" as used in this invention means water solubility in the zinc oxide-water slurry at the concentrations used for catalyzing the reaction between the zinc oxide and phosphorous acid. In addition, these water soluble organic carboxylic acids may contain other functional groups such as hydroxyl, amino or carbonyl. Among the catalysts useful in this invention are formic acid, acetic acid, propionic acid, butyric acid, maleic acid, citric acid, lactic acid, levulinic acid and the like. Inorganic acids such as nitric acid and sulfamic acid may also be used. Acetic acid is preferred however because it is inexpensive and readily available.

The amount of catalyst preferred is between 0.2% and 1% based on the weight of ZnO in the slurry. Amounts greater than 1% offer no useful function in improving yields and purities of the basic zinc phosphites.

The phosphorous acid admixed with the zinc oxide slurry can be any strength phosphorous acid, either anhydrous or in aqueous solution. It is preferred to use from 50% to 70% aqueous phosphorous acid since it is readily available and can be easily handled.

In order to prepare the basic zinc phosphites of this invention the number of moles of phosphorous acid must be from 1/1.5 to 1/11 the number of moles of zinc oxide. To determine the molar amount of phosphorous acid required to prepare any given basic zinc phosphite the following relationship may be used:

$$[H_3PO_3] = \frac{[ZnO]}{(X+1)}$$

wherein $[H_3PO_3]$ is the number of moles of phosphorous acid; $[ZnO]$ is the number of moles of zinc oxide; and X is the basicity of the basic zinc phosphite to be prepared. For example, if it is desired to prepare monobasic zinc phosphite (X = 1) using 1 mole of zinc oxide in the slurry, ½ mole of phosphorous acid (100%) would be required. If tetrabasic zinc phosphite (X = 4) is desired using 1 mole of zinc oxide, then 1/5 mole of phosphorous acid would be required.

The phosphorous acid should be added slowly to the zinc-oxide-water slurry under constant agitation to prevent agglomeration of the formed basic zinc phosphite with the zinc oxide. Preferably this is accomplished by dropwise acid addition over a period of 45 to 60 minutes.

After all phosphorous acid has been added, the slurry may be heated while stirring to accelerate reaction. Generally heating at 65° to 85°C. for from 1 to 5 hours is sufficient to convert all zinc oxide and phosphorous acid to basic zinc phosphite. The slurry may be maintained at room temperatures, however longer reaction times are required.

The basic zinc phosphites form as a white solid which can be recovered by filtering. The product is then dried in an oven at from 100° to 120°C. If anhydrous basic zinc phosphites are desired, heating is continued at higher temperatures.

It has been found that yields of basic zinc phosphite of from 96 to 98% are achieved using this process based on the amount of zinc oxide used.

In order to more fully describe the instant invention the following examples are given:

EXAMPLE 1

This example illustrates the preparation of tribasic zinc phosphite, ($3ZnO . ZnHPO_3 . 2H_2O$).

Exactly 209.35 g of zinc oxide was stirred into 1500 ml of water at room temperature. To the uniform slurry was added 6.25 ml of 10% acetic acid. Then 76.28 g of 69% phosphorous acid was added dropwise over a period of 1 hour during which time the temperature rose 27°C. The slurry temperature was then raised to 65°C. and stirring was continued for 3 hours at between 65–70°C. The pH of the mixture was 6.65. The reaction mixture was then vacuum filtered and the product was dried for 18 hours at 105°C. The actual yield of product was 269.78 g. Theoretical yield was 273.18 g. Analysis of the product showed: % Zn (observed), 61.90% Zn (theoretical), 61.46%; % P (observed), 7.24%, % P (theoretical) 7.28%, moles Zn/P (theoretical, 4.00; moles Zn/P (observed) 4.05.

EXAMPLES 2–10

In these examples basic zinc phosphites were prepared using the procedure of Example 1 having basicities ranging from 1 to 2 and 4 to 10. Table 1 below lists the amounts of zinc oxide, water, 10% acetic acid and phosphorous acid used in the preparations.

TABLE 1

| Basic Zinc Phosphite | Formula | ZnO (g) | Water (ml) | 10% Acetic Acid (ml) | 69% $H_3PO_3$ (g) | 75.7% $H_3PO_3$ (g) | 100% $H_3PO_3$ (g) | % Zn (Theor) | % Zn (Obs) | % P (Theor) | % P (Obs) |
|---|---|---|---|---|---|---|---|---|---|---|---|
| Monobasic | $ZnO.ZnHPO_3.1H_2O$ | 167.50 | 750 | 5.0 | | 111.24 | | 53.42 | 52.70 | 12.66 | 12.80 |
| Dibasic | $2 ZnO.ZnHPO_3.2H_2O$ | 315.57 | 1000 | 9.5 | | | 106.5 | 56.99 | 56.90 | 8.90 | 9.01 |
| Tetrabasic | $4 ZnO.ZnHPO_3.2H_2O$ | 346.34 | 2530 | 10.4 | 100.96 | | | 64.49 | 63.80 | 6.11 | 5.95 |
| Pentabasic | $5 ZnO.ZnHPO_3.2H_2O$ | 177.19 | 1000 | 5.3 | | 39.23 | | 66.68 | 66.15 | 5.27 | 5.67 |
| Hexabasic | $6 ZnO.ZnHPO_3.2H_2O$ | 180.17 | 1000 | 5.4 | | 34.19 | | 67.43 | 67.70 | 4.57 | 4.63 |
| Heptabasic | $7 ZnO.ZnHPO_3.2H_2O$ | 182.47 | 1000 | 5.5 | | 30.30 | | 68.81 | 68.67 | 4.08 | 3.83 |
| Octabasic | $8 ZnO.ZnHPO_3.2H_2O$ | 184.48 | 1000 | 5.5 | | 27.21 | | 69.93 | 70.00 | 3.68 | 3.73 |
| Nonabasic | $9 ZnO.ZnHPO_3.2H_2O$ | 185.80 | 800 | 5.6 | | 24.68 | | 71.54 | 71.68 | 3.39 | 3.06 |
| Decabasic | $10 ZnO.ZnHPO_3.2H_2O$ | 187.04 | 800 | 5.6 | | 22.59 | | 72.26 | 72.08 | 3.11 | 2.73 |

EXAMPLE 11

This example illustrates the performance of the basic zinc phosphites of this invention for inhibiting tannin staining of cedar surfaces coated with a latex paint containing the basic zinc phosphites.

In the procedure, a series of acrylic latex paints were formulated containing the basic zinc phosphites prepared in Examples 1 through 10. As controls, a basic lead sulfo-silicate complex and a normal zinc phosphite were also formulated in the latex formulations which had the following composition:

| INGREDIENTS | PARTS BY WEIGHT |
|---|---|
| Water | 260.00 |
| Thickener (Bentone LT-NL Industries, Inc.) | 4.00 |
| Potassium Tripolyphosphate | 2.00 |
| Dispersant (Tamol 850-Rohm & Haas Co.) | 13.00 |
| Wetting Agent (Triton X-100 Rohm & Haas Co.) | 6.00 |
| Antifoam Agent (Colloids 677-Colloids, Inc.) | 2.00 |
| Phenyl Mercuric Borate | 0.40 |
| Titanium Dioxide Pigment | 190.00 |
| Acrylic Emulsion (46% resin solids) | 450.00 |
| Coalescent Agent | 6.00 |
| Ethylene Glycol | 40.00 |
| Ammonium Hydroxide | 1.70 |
| Tannin Stain Inhibitor or Controls | 150.00 |

A cedar panel was coated with the above acrylic latexes to form side by side vertically painted strips approximately 3½ inches wide. The spreading rate was 450 square feet per gallon. An identical latex formulation which contained no tannin stain inhibitor was also applied to the panel as a control. After the latex coatings dried (about 2 hours) a top coat of a commercial acrylic latex-based paint was applied to the dried latex film.

After drying overnight the cedar panel was placed in a Cleveland High Humidity Cabinet for 72 hours. The panels were then visually observed for overall tannin staining of the top coated surfaces. The difference in color of the top coat indicated whether or not cedar staining was effectively inhibited. The results are summarized in Table 2 below.

TABLE 2

| Example | Tannin Stain Inhibitor | Inhibition of Tannin Staining |
|---|---|---|
| Control | Normal zinc phosphite | Not effective |
| 1 | Tribasic Zinc phosphite | effective |
| 2 | Monobasic zinc phosphite | Slightly effective |
| 3 | Dibasic zinc phosphite | effective |
| 4 | Tetrabasic zinc phosphite | effective |
| 5 | Pentabasic zinc phosphite | effective |
| 6 | Hexabasic zinc phosphite | effective |
| 7 | Heptabasic zinc phosphite | effective |
| 8 | Octabasic zinc phosphite | effective |
| 9 | Nonabasic zinc phosphite | Moderately effective |
| 10 | Decabasic zinc phosphite | Moderately effective |
| Control | Basic lead sulfo-silicate complex | effective |
| Control | None | Not effective |

As the table shows the monobasic zinc phosphite begins to show effective tannin stain inhibition whereas normal zinc phosphite is not effective. The tribasic thru octabasic zinc phosphites are as effective as the basic lead sulfo-silicate complex. The nona and decabasic zinc phosphites are also effective but to a moderate degree as compared to the tribasic tru octabasic zinc phosphites.

EXAMPLE 12

In this example, an acrylic latex paint modified with an alkyd was formulated containing tribasic zinc phosphite as a tannin stain inhibitor. The same latex was formulated using a basic lead sulfo-silicate complex as a control tannin stain inhibitor. The latex formulations had the following general composition;

| INGREDIENTS | PARTS BY WEIGHT |
|---|---|
| Water | 292.00 |
| Thickener (Bentone LT-NL Industries, Inc.) | 2.00 |
| Dispersant (Tamol 850-Rohm & Haas Co.) | 13.00 |
| Potassium Tripolyphosphate | 2.00 |
| Anti-Foam Agent (Nopco NXZ-Nopco-Chem. Co.) | 2.00 |
| Ethylene Glycol | 40.00 |
| Preservative (Super-Ad-It, Tenneco Chemicals Inc.) | 1.80 |
| Titanium Dioxide Pigment | 160.00 |
| Acrylic Emulsion (50% resin solids) | 400.00 |
| Alkyd Modified With Metallic Driers | 25.00 |
| Coalescent Agent (Tributyl Phosphate) | 10.00 |
| Tannin Stain Inhibitor | 140.00 |

Using the procedure of Example 11 for coating cedar panels with the latex formulations the top coatings were examined for overall cedar stain inhibition both before and after 72 hours of high humidity testing. The results are summarized in Table 3 below.

TABLE 3

| TANNIN STAIN INHIBITOR | INHIBITION OF TANIN STAINING | |
|---|---|---|
| | Before High Humidity | After 72 hrs in High Humidity |
| A. Tribasic zinc phosphite | effective | effective |
| B. Basic lead sulfo-silicate complex | effective | effective |

As the table shows, tribasic zinc phosphite exhibits comparable tannin stain inhibition compared to the basic lead sulfo-silicate complex in the latex used.

EXAMPLE 13

In this example a polyvinyl acetate copolymer latex paint was formulated containing tribasic zinc phosphite as a tannin stain inhibitor. The same type latex was also formulated containing a basic lead sulfo-silicate complex as a control tannin stain inhibitor. The latex formulations had the following general composition;

| INGREDIENT | PARTS BY WEIGHT |
|---|---|
| Water | 275.00 |
| Dispersant (Tamol 850-Rohm & Haas Co.) | 13.00 |
| Thickener (Bentone LT-NL Industries, Inc.) | 2.00 |
| Anti Foam Agent (Polyglycol P-1200, Dow Chemical) | 2.50 |
| Wetting Agent (Tergitol NPX, Union Carbide) | 6.00 |
| Butyl cellosolve acetate | 12.00 |
| Ethylene Glycol | 40.00 |
| Titanium Dioxide Pigment | 140.00 |

| INGREDIENT | PARTS BY WEIGHT |
| --- | --- |
| Phenyl mercuric borate | 0.40 |
| Vinyl Acetate Copolymer Emulsion (51% resin solids) | 450.00 |
| Tannin Stain Inhibitor | 140.00 |

Using the procedure of Example 11 for coating cedar panels with the latex formulations the dried strips were examined for overall cedar stain inhibition both before and after 72 hours of high humidity testing.

The results are summarized in Table 4 below.

TABLE 4

| | TANNIN STAIN INHIBITOR | INHIBITION OF TANNIN STAINING | |
| --- | --- | --- | --- |
| | | Before High Humidity | After 72 hrs. in High Humidity |
| C. | Tribasic zinc phosphite | effective | moderately effective |
| D. | Basic lead sulfo-silicate complex | effective | effective |

The results show that tribasic zinc phosphite is comparable to the basic lead sulfo-silicate complex.

EXAMPLE 14

This example illustrates the preparation of tribasic zinc phosphite, $3 ZnO \cdot ZnHPO_3 \cdot 2H_2O$ by employing various acid catalysts in the zinc oxide slurry.

A series of experiments were conducted following the procedure of Example 1 except that in each experiment acetic acid was replaced with a different acid catalyst. Table 5 below summarizes the types and amounts of catalyst used in the experiments. All amounts of catalyst are expressed as a weight percent of the zinc oxide used in the slurry. Yields of tribasic zinc phosphite formed were substantially the same as in Example 1.

TABLE 5

| Experiment | Type of Catalyst | Amount of Catalyst(wt.%) |
| --- | --- | --- |
| E | Formic acid | 0.23 |
| F | Lactic acid | 0.45 |
| G | Levulinic acid | 0.58 |
| H | Nitric acid | 0.30 |
| I | Propionic acid | 0.37 |
| J | Sulfamic acid | 0.48 |

EXAMPLE 15

This example illustrates the preparation of tribasic zinc phosphite wherein the zinc oxide slurry is added to a phosphorous acid solution.

Zinc oxide, 209.35g. was slurried with 765 ml of deionized water and 6.25 ml of 10% acetic acid. A phosphorous acid solution was made-up by adding 75.97 g. of 69.28% aqueous phosphorous acid to 600 ml of water. The zinc oxide slurry was then slowly added to the phosphorous acid solution with stirring over a period of 55 minutes. Stirring was continued for 5 hours at between 20° and 88°C. The final pH was 6.88. The solids were recovered by filtering and drying at 120°C. Yield and analysis of the product was substantially the same as in Example 1.

EXAMPLE 16

This example illustrates the preparation of tribasic zinc phosphite wherein no catalyst is employed.

French process zinc oxide, 208.93g. and 1500 ml of water were mixed together at ambient temperature. To this was slowly added 76.28g. of 69% phosphorous acid over a period of 1 hour. The mixture was then heated to between 65°–70°C and stirring continued for about 1 hour. The final pH was 6.62. The solids were recovered by vacuum filtering, drying 20 hours at 105°C and hammer-milling through a 0.02 inch perforated screen. The yield of dried product was 269.7g. Elemental analysis of the product showed:

% Zn; 61.90; %P, 7:26; moles Zn/P, 3.98.

EXAMPLE 17

This example illustrates the ineffectiveness of a physical blend of 3 moles of ZnO and 1 mole of $ZnHPO_3$, corresponding to the compound tribasic zinc phosphite ($3 ZnO \cdot ZnHPO_3$) in inhibiting tannin staining of a wood surface.

In this procedure, four acrylic latex paint formulations were prepared each containing different tannin stain inhibitor candidates: the first containing a physical blend of 50.4 parts by weight of normal zinc phosphite and 84.5 parts by weight of zinc oxide (molar ratio of $ZnO/ZnHPO_3$ was 3/1). The 135 contained 135 parts by weight of tribasic zinc phosphite as prepared in Example 1.

The latex formulations had the following composition:

| INGREDIENTS | PARTS BY WEIGHT |
| --- | --- |
| Water | 230.0 |
| Thickener (Bentone LT-NL Industries, Inc.) | 5.0 |
| Potassium Tripolyphosphate | 1.0 |
| Dispersant (DAXAD 30-Dewey & Almy Co.) | 6.5 |
| Wetting Agent (Triton X-100-Rohm & Haas) | 4.5 |
| Phenyl mercuric borate | 2.0 |
| Anti Foam Agent (Colloids 667-Colloids Inc.) | 2.0 |
| Titanium Dioxide Pigment | 220.0 |
| Composite Extender Pigment | 40.0 |
| Acrylic Emulsion (46% resin solids) | 520.0 |
| Coalescent Agent | 7.0 |
| Ethylene Glycol | 30.0 |
| Ammonium hydroxide | 2.0 |
| Tannin Stain Inhibitor Candidate | 135.0 |

The procedure for coating cedar panels as outlined in Example 11 was used to test the tannin stain inhibitory characteristics of the candidates. Table 6 below summarizes the results.

TABLE 6

| Tannin Stain Inhibitor Candatate | Inhibition of Tannin Staining |
| --- | --- |
| K Physical Blend of $3ZnO/ZnHPO_3$ | ineffective |
| L ZnO | ineffective |
| M $ZnHPO_3$ | ineffective |
| N $3 ZnO \cdot ZnHPO_3 \cdot 2H_2O$ | effective |

As the table shows, the physical blend of zinc oxide and zinc phosphite, zinc oxide alone or zinc phosphite alone are ineffective tannin stain inhibitors while the tribasic zinc phosphite of this invention is completely effective.

EXAMPLE 18

This example illustrates the effective tannin stain inhibition of a non-hydrated tribasic zinc phosphite, 3 $ZnO \cdot ZnHPO_3$.

The tribasic zinc phosphite of Example 1 heated in an oven at about 300°C for several hours to remove all water of hydration. Using the procedure of Example 11, the resulting dehydrated tribasic zinc phosphite was incorporated into the latex paint formulation and tested for tannin stain inhibition on a cedar panel. The effectiveness of tannin stain inhibition was substantially the same as the hydrated tribasic zinc phosphite of Example 1.

EXAMPLE 19

This example illustrates the preparation of hemibasic zinc phosphite (½ $ZnO \cdot ZnHPO_3 \cdot 1 H_2O$).

Exactly 131.48g. of zinc oxide were slurried in 500 ml of 67°C water and 3.9 ml of 10% acetic acid. Then 82.94g of 106.3% phosphorous acid were diluted with 80 ml of water. The phosphorous acid solution was slowly added to the stirred 60°–67°C zinc oxide slurry in 75 minutes and stirring was continued for 45 minutes at 65°–70°C. The slurry was allowed to stand for several hours at ambient temperature (pH 6.89). The solids were recovered by vacuum filtering and drying at 105°C. Total yield was 419g.

| Wet analysis | Observed | Calculated |
|---|---|---|
| %Zn | 48.8 | 49.14 |
| %P | 15.8 | 15.55 |
| moles Zn/P | 1.50 | 1.50 |

EXAMPLE 20

This example illustrates the corrosion inhibiting properties of tribasic zinc phosphite when applied to a wood surface containing iron nail heads flush to the surface.

The latex paint formulations of Examples 11, 12 and 13 containing tribasic zinc phosphite as prepared in Example 1 were coated on white pine beveled siding which contained six iron nails driven flush to the surface to the pine boards. As a control the same board was coated side by side with similar latexes which contained no tribasic zinc phosphite. The boards were exposed north and south on vertical test fences outdoors. The condition of the nail heads were observed after 5 days exposure and after 26 days exposure using corrosion ratings as are set forth in ASTM D610-68 i.e. 10=no rust; 1–100% rust. Table 7 below summarizes the results.

TABLE 7

| | | Corrosion Ratings | | | |
|---|---|---|---|---|---|
| | | Exposure South | | Exposure North | |
| Board | Latex Formulaton | 5 days | 26 days | 5 days | 26 days |
| O | Example 11 | 9 | 9 | 9 | 9 |
| P | Example 11 Control | 4 | 4 | 7 | 4 |
| Q | Example 13 | 10 | 10 | 10 | 9 |
| R | Example 13 Control | 5 | 4 | 5 | 3 |
| S | Example 12 | 9 | 9 | 10 | 10 |
| T | Example 12 Control | 5 | 4 | 7 | 5 |

As the results in the table show, corrosion inhibition is imparted to each latex coating containing tribasic zinc phosphite. The controls, on the other hand, show substantial nail head corrosion in almost all cases.

EXAMPLE 21

Three oleoresinous paints, oil-alkyd vehicle were formulated with equal volumes of hemi-basic zinc phosphite, monobasic zinc phosphite and dibasic zinc phosphite respectively. The control paints were made with dibasic lead phosphite, a well known anti-corrosive pigment, and a blank where the volume of anti-corrosive pigment was replaced with magnesium silicate. The paints were coated on sand blasted clean steel and rusted hot-rolled steel panels. Each paint was applied to the steel panels as single coats and double coats. The control paints were coated on identical steel panels. These panels were then exposed to a marine atmosphere at Ocean City, N.J. After 20 months exposure the panels were evaluated for corrosion inhibition using the corrosion ratings of ASTM D610-68; 10=rust; 1=100% rust. The results are noted in Table 8.

TABLE 8

| | | One Coat | | Two Coats | |
|---|---|---|---|---|---|
| Test | Corrosion Inhibitor | Clean Steel | Rusted Steel | Clean Steel | Rusted Steel |
| U | Hemibasic Zinc Phosphite | 8 | 9 | 9 | 9 |
| V | Monobasic Zinc Phosphite | 7 | 1(1) | 9 | 6 |
| W | Dibasic Zinc Phosphite | 7 | 9 | 9 | 9 |
| X | Control (Dibasic lead phosphite) | 5 | 9 | 9 | 9 |
| Y | Blank | 1(2) | 1(2) | 7(3) | 4(3) |

(1)After eleven months exposure
(2)After three months exposure
(3)After six months exposure

EXAMPLE 22

One coat of the same paints as in Example 21 were applied to No. 100 Bonderized steel panels exposed to salt fog for 300 hours according to ASTM B117-64 and evaluated according to ASTM D714-56; Evaluating Degree of Blistering of Paints.

Table 9 summarizes the results of the salt fog tests.

TABLE 9

| Corrosion Inhibitor | Rating after 300 hours |
|---|---|
| Test U¹-Hemibasic Zinc Phosphite | 8M |
| Test V¹-Monobasic Zinc Phosphite | 8M |
| Test W¹-Dibasic Zinc Phosphite | 8M |
| Test X¹-Control(Dibasic lead phosphite) | 8F |
| Test Y¹-Blank | F(100 hours) |

8M = medium amount of very small blisters
8F = few very small blisters
F = failed — large blisters The formulation for the test paints of Examples 21 and 22 was as follows:

| INGREDIENT | GALLONS |
| --- | --- |
| Corrosion Inhibitor | 1.34 |
| Titanium Dioxide | 5.29 |
| Magnesium Silicate | 18.44 |
| Thickening and Suspending Agent (Bentone 38-NL Industries, Inc.) | 0.27 |
| Raw Linseed Oil | 20.26 |
| Alkyd Resin Solution (TT-R-266D Type I class B) | 28.03 |
| Mineral Spirits — medium | 25.25 |
| Anti-skinning Agent | 0.13 |
| Driers | 0.80 |
| Total | 99.81 |

EXAMPLE 23

This example illustrates the mildew resistant properties of a latex paint containing tribasic zinc phosphite.

The latex paint of Example 11 containing the tribasic zinc phosphite as was prepared according to Example 1, was coated on cedar beveled siding and the siding exposed 90° south at Hightstown, N.J. As a control a similar latex was coated on the siding containing no tribasic zinc phosphite.

At the end of 2, 4, and 6 months, the coated siding surface was examined for the presence of mildew growth. Mildew resistance was rated numerically from 1 to 10; a rating of 10 indicated no mildew growth and a rating of 0 indicated substantial mildew growth.

The results are summarized in Table 10.

TABLE 10

| | Mildew Resistance | | | | | |
| --- | --- | --- | --- | --- | --- | --- |
| | 90° North | | | 90° South | | |
| Sample | 2 mos. | 4 mos. | 6 mos. | 2 mos. | 4 mos. | 6 mos. |
| Tribasic zinc phosphite | 10 | 10 | 10 | 10 | 10 | 10 |
| Control | 10 | 10 | 9 | 10 | 8 | 7 |

As the results indicate tribasic zinc phosphite imparted long term mildew resistance to the coating.

EXAMPLE 24

This example illustrates the flame-retardant properties of tribasic zinc phosphite in a flammable plastic composition.

A flammable polyester composition was prepared by combining the following ingredients:

| INGREDIENT | Weight |
| --- | --- |
| Polyester of a polybasic alcohol with saturated and unsaturated polybasic acids | 50.0 g |
| Halogenated polyester | 50.0 g |
| Cobalt napthenate | 0.2 g |
| Peroxide of methyl ethyl ketone | 1.7 g |
| Tribasic zinc phosphite | 8.0 g |

A sample of the composition was held vertically in a cylinder. Mixtures of oxygen and nitrogen gasses were allowed to rise and pass over the sample. The lowest percentage of oxygen at which the sample burned for 3 minutes after ignition was recorded as the oxygen index. As a control, a flammable polyester composition was prepared containing no tribasic zinc phosphite and tested.

The oxygen index of the tribasic zinc phosphite-containing polyester composition was 24.6. The same polyester containing no tribasic zinc phosphite had an oxygen index of 21.6. These results show that tribasic zinc phosphite imparts flame retardancy to flammable materials.

We claim:

1. In a latex paint coating composition, the improvement comprising having present in said latex paint coating composition an agent for rendering said latex paint coating composition color resistant toward tannin stains and possessing corrosion and mildew resistant properties, said agent comprising a basic zinc phosphite having the formula X ZnO.ZnHPO$_3$ where X is a number from ½ to 100

2. Latex paint coating composition according to claim 1 in which the basic zinc phosphite contains from 0 to 3 moles of bound water.

3. A process for imparting tannin stain inhibition, corrosion resistance and mildew resistance to a latex paint coating composition which comprises adding to said latex paint coating composition a basic zinc phosphite, said basic zinc phosphite having the formula X ZnO.ZnHPO$_3$ where X is a number from ½ to 10.

* * * * *